US008668690B2

(12) United States Patent
Couture

(10) Patent No.: US 8,668,690 B2
(45) Date of Patent: Mar. 11, 2014

(54) APPARATUS AND METHOD FOR OPTIMAL TISSUE SEPARATION

(75) Inventor: Gary M. Couture, Longmont, CO (US)

(73) Assignee: Covidien LP, Mansfield, MA (US)

( * ) Notice: Subject to any disclaimer, the term of this patent is extended or adjusted under 35 U.S.C. 154(b) by 951 days.

(21) Appl. No.: 12/793,136

(22) Filed: Jun. 3, 2010

(65) Prior Publication Data
US 2011/0301607 A1 Dec. 8, 2011

(51) Int. Cl.
*A61B 18/12* (2006.01)

(52) U.S. Cl.
USPC .................................. 606/51; 606/34

(58) Field of Classification Search
USPC ............................ 606/37–40, 50–52; 607/99
See application file for complete search history.

(56) References Cited

U.S. PATENT DOCUMENTS

| 4,191,188 | A | 3/1980 | Belt et al. |
| 4,378,801 | A | 4/1983 | Oosten |
| 4,429,694 | A | 2/1984 | McGreevy |
| 4,438,766 | A | 3/1984 | Bowers |
| 4,559,943 | A | 12/1985 | Bowers |
| 6,033,399 | A | 3/2000 | Gines |
| 6,692,489 | B1 | 2/2004 | Heim et al. |
| 7,137,980 | B2 | 11/2006 | Buysse et al. |
| 7,175,621 | B2 | 2/2007 | Heim et al. |
| RE40,388 | E | 6/2008 | Gines |
| D574,323 | S | 8/2008 | Waaler |
| 2007/0038209 | A1 | 2/2007 | Buysse et al. |
| 2007/0173811 | A1* | 7/2007 | Couture et al. ............ 606/39 |
| 2008/0315684 | A1* | 12/2008 | Cheng et al. ............ 307/45 |
| 2009/0082765 | A1* | 3/2009 | Collins et al. ............ 606/38 |
| 2009/0248007 | A1 | 10/2009 | Falkenstein et al. |
| 2010/0049261 | A1* | 2/2010 | Bare ........................... 607/1 |
| 2010/0179534 | A1 | 7/2010 | Podhajsky et al. |
| 2010/0179535 | A1 | 7/2010 | Podhajsky et al. |

FOREIGN PATENT DOCUMENTS

| DE | 179607 | 3/1905 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |

(Continued)

OTHER PUBLICATIONS

U.S. Appl. No. 10/406,690, filed Apr. 3, 2003.

(Continued)

*Primary Examiner* — Michael Peffley
*Assistant Examiner* — Thomas Giuliani

(57) ABSTRACT

A system and method for optimizing tissue separation using modulated or duty cycle controlled waveforms on desiccated tissue, where the desiccated tissue has a high electrical impedance. In bipolar electrosurgical procedures, tissue separation is separated with the application of an electrical signal. When tissue does not completely separate and becomes desiccated, generator may generate a duty cycle controlled waveform with specified duty cycle and frequency or modulated waveform. Modulated waveform is generated by adding or multiplying one or more waveforms together. Modulated or duty cycle waveforms create power pulses with higher voltages and a low RMS value. Power pulses drive power and create heat in the high impedance tissue. The creation of heat helps to mobilize water content adjacent to the desiccated tissue. The heating and mobilization of water induces motion into the tissue and aids in the complete separation of tissue while keeping the RMS power low.

8 Claims, 4 Drawing Sheets

(56) References Cited

FOREIGN PATENT DOCUMENTS

| | | |
|---|---|---|
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1472984 | 11/2004 |
| EP | 1366724 | 1/2006 |
| EP | 880220 | 6/2006 |
| EP | 1776929 | 4/2007 |
| EP | 2111812 | 10/2009 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |
| WO | WO2008/053532 | 5/2008 |

OTHER PUBLICATIONS

U.S. Appl. No. 10/573,713, filed Mar. 28, 2006.
U.S. Appl. No. 10/761,524, filed Jan. 21, 2004.
U.S. Appl. No. 11/242,458, filed Oct. 3, 2005.
U.S. Appl. No. 12/534,308, filed Aug. 3, 2009.
U.S. Appl. No. 12/540,190, filed Aug. 12, 2009.
U.S. Appl. No. 12/549,563, filed Aug. 28, 2009.
U.S. Appl. No. 12/556,770, filed Sep. 10, 2009.
U.S. Appl. No. 12/566,173, filed Sep. 24, 2009.
U.S. Appl. No. 12/566,233, filed Sep. 24, 2009.
U.S. Appl. No. 12/567,966, filed Sep. 28, 2009.
U.S. Appl. No. 12/613,876, filed Nov. 6, 2009.
U.S. Appl. No. 12/619,234, filed Nov. 16, 2009.
U.S. Appl. No. 12/639,210, filed Dec. 16, 2009.
U.S. Appl. No. 12/712,712, filed Feb. 25, 2010.
U.S. Appl. No. 12/713,956, filed Feb. 26, 2010.
U.S. Appl. No. 12/715,212, filed Mar. 1, 2010.
U.S. Appl. No. 12/793,136, filed Jun. 3, 2010.
U.S. Appl. No. 12/823,703, filed Jun. 25, 2010.
U.S. Appl. No. 12/826,879, filed Jun. 30, 2010.
U.S. Appl. No. 12/834,364, filed Jul. 12, 2010.
U.S. Appl. No. 12/845,203, filed Jul. 28, 2010.
U.S. Appl. No. 12/902,287, filed Oct. 12, 2010.
Wald et al., "Accidental Burns", JAMA, Aug. 16, 1971, vol. 217, No. 7, pp. 916-921.
Vallfors et al., "Automatically Controlled Bipolar Electrosoagulation—'COA—COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192—Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.

(56) References Cited

OTHER PUBLICATIONS

International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
Examiner's First Report issued in corresponding Australian Appln. No. 2011202594 dated Aug. 8, 2011.
European Search Report for European Application No: 11168660 dated Oct. 10, 2011.

\* cited by examiner

APPARATUS AND METHOD FOR OPTIMAL TISSUE SEPARATION

BACKGROUND

1. Technical Field

The present disclosure relates to an electrosurgical system and method and, more particularly, to duty cycle controlled waveforms and modulated waveforms for use in optimizing tissue separation.

2. Background of Related Art

Energy-based tissue treatment is well known in the art. Various types of energy (e.g., electrical, ohmic, resistive, ultrasonic, microwave, cryogenic, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes.

During the cutting process, the generator supplies an electrical signal at a fixed sinusoidal frequency to an electrosurgical instrument to cut the tissue. Occasionally, the tissue will not completely separate and become completely desiccated because the tissue dries or loses moisture as the electrical signal is applied to the tissue. The desiccated tissue has a very high electrical impedance. An object of the invention is to provide modulated or duty cycle controlled waveforms with higher voltages to completely separate the tissue while keeping the root mean square (RMS) power low.

SUMMARY

A system and method for optimizing tissue separation using modulated or duty cycle controlled waveforms on desiccated tissue, where the desiccated tissue has a high electrical impedance. In bipolar electrosurgical procedures, tissue separation is separated with the application of an electrical signal. When tissue does not completely separate and becomes desiccated, a generator may generate a duty cycle controlled waveform with a specified duty cycle and frequency or a modulated waveform. The modulated waveform is generated by adding or multiplying one or more waveforms together. The modulated or duty cycle controlled waveforms create power pulses with higher voltages and a low RMS value. The power pulses drive power and create heat in the high impedance tissue. The creation of heat helps to mobilize water content adjacent to the desiccated tissue. The heating and mobilization of water induces motion into the tissue and aids in the complete separation of tissue while keeping the RMS power low.

According to an embodiment of the present disclosure, a method for optimizing tissue separation including the steps of grasping a section of tissue with an electrosurgical instrument and sending a pulse waveform to the instrument to seal the tissue. The method further includes the steps of sending a sinusoidal waveform to the instrument to cut the tissue and determining if the tissue is completely separated. In response to determining the tissue is not completely separated, the method further includes the step of generating a duty cycle controlled waveform or a modulated waveform. The duty cycle controlled and the modulated waveform have a larger voltage than the sinusoidal waveform used to cut the tissue and a low root mean square (RMS) power value. The method then sends the duty cycle controlled or the modulated waveform to the instrument to completely separate the tissue.

According to another embodiment of the present disclosure, a method for performing a surgical procedure includes the step of grasping a section of tissue with an electrosurgical instrument and sending a pulse waveform to the instrument to seal the tissue. The method also includes the steps of sending a sinusoidal waveform to the instrument to cut the tissue and determining if the tissue is completely separated. In response to determining the tissue is not completely separated, the method further includes the step of generating with a generator a duty cycle controlled waveform from pulsing a fundamental frequency at a specified duty cycle. The duty cycle controlled waveform has a larger voltage than the sinusoidal waveform used to cut the tissue and a low root mean square (RMS) power value. The method then sends the duty cycle controlled waveform to the instrument to completely separate the tissue.

According to another embodiment of the present disclosure, a system for performing a surgical procedure includes an electrosurgical instrument configured to grasp a section of tissue and a generator. The generator is configured to selectively supply an electrical signal to the electrosurgical instrument in three phases. In a first phase, the generator sends a pulsed waveform to the electrosurgical instrument to seal the tissue. In a second phase, the generator sends a sinusoidal waveform to the instrument to cut the tissue. In a third phase, the generator sends a duty controlled waveform or a modulated waveform to cut unseparated tissue with a larger voltage than the sinusoidal waveform used to cut the tissue and a low root mean square (RMS) power value.

Further, the generator can automatically initiate the third phase upon determining the tissue separation in the second phase was unsuccessful. A sensor determines an electrical impedance of the cut tissue. Alternatively, a user may be alerted to the unsuccessful tissue separation in the second phase. The user is then prompted to initiate the generator to supply energy using the third phase.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The generator according to the present disclosure can perform bipolar electrosurgical procedures, including vessel sealing procedures. The generator may include a plurality of outputs for interfacing with various electrosurgical instruments (e.g., bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., bipolar, vessel sealing).

Figure 1:
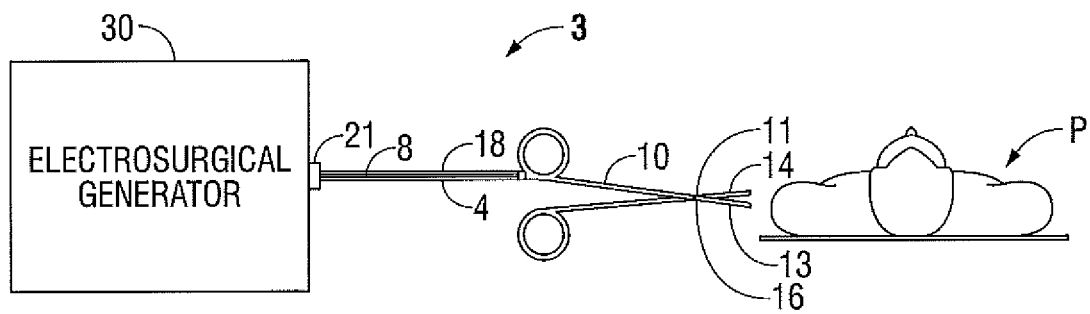
FIG. 1 is a schematic block diagram of a bipolar electrosurgical system in accordance with an embodiment of the present disclosure.

FIG. 1 is a schematic illustration of a bipolar electrosurgical system according to the present disclosure. The system includes bipolar electrosurgical forceps 10 having one or more electrodes for treating tissue of a patient P. The electrosurgical forceps 10 include, opposing jaw members 11 and 16 having an active electrode 14 and a return electrode 13, respectively, disposed therein. The active electrode 14 and the return electrode 13 are connected to the generator 30 through cable 18, which includes the supply and return lines 4, 8 coupled to the active terminal 31 and return terminal 32, respectively (see FIG. 3). The electrosurgical forceps 10 are coupled to the generator 30 at a connector 21 having connections to the active terminal 31 and return terminal 32 (e.g., pins) via a plug disposed at the end of the cable 18, wherein the plug includes contacts from the supply and return lines 4, 8.

The generator 30 includes suitable input controls (e.g., buttons, activators, switches, touch screen, etc.) for controlling the generator 30. In addition, the generator 30 may include one or more display screens for providing the user with variety of output information (e.g., intensity settings, treatment complete indicators, etc.). The controls allow the user to adjust power of the RF energy, waveform parameters including a fundamental frequency, a beat frequency, duty cycle, and/or other parameters to achieve the desired waveform suitable for a particular task (e.g., coagulating, tissue sealing, intensity setting, etc.).

Figure 2:
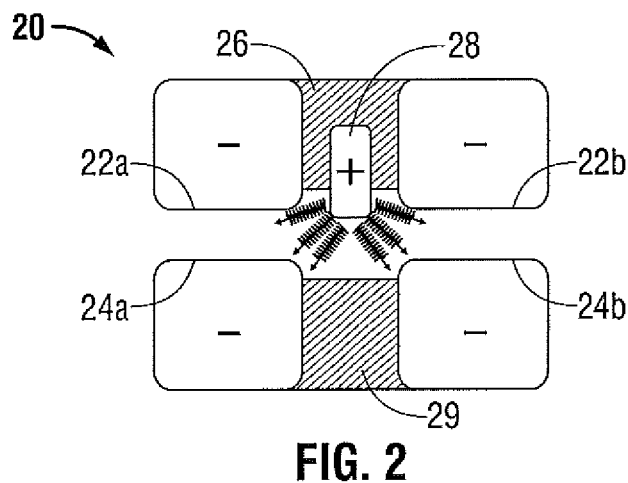
FIG. 2 is an enlarged, schematic end view showing one embodiment of an electrode assembly of the present disclosure.

FIG. 2 is an enlarged, schematic end view showing one embodiment of an electrode assembly 20 of the present disclosure. During the so called "sealing phase", the jaw members 11 and 16 are closed about tissue and the cutting element 26 may be configured to form a requisite gap between opposing sealing surfaces 22a, 24a, and 22b, 24b. During activation of the sealing phase, the cutting element 26 is not necessarily energized such that the majority of the current is concentrated between diametrically opposing sealing surfaces between 22a and 24a and 22b and 24b to effectively seal the tissue. Additionally, stop members (not shown) may be disposed on the sealing surfaces, adjacent to the sealing surfaces, or on the insulators 28, 29 to regulate the gap distance between opposing sealing surfaces 22a, 24a and 22a, 24b.

The electrode assembly 20 in this embodiment only includes one cutting element 26. The cutting element 26 is disposed opposite insulator 29 which provides a dual function during activation of the electrode assembly 20: 1) provides a uniform gap between sealing surfaces 22a and 24a and 22b and 24b during the sealing phase (eliminating a need for the above-mentioned stop members); and 2) prevents the electrode 20 from shorting during the sealing and cutting phases. During activation, the cutting element 26 is energized to a first potential "+" and the opposing sealing surfaces 22a, 24a, and 22b, 24b are energized to a second electrical potential "−" which creates an area of high power density between the two previously formed tissue seals and cuts the tissue. Additionally, FIG. 2 is one example of electrode assembly 20, other embodiments of electrode assemblies are disclosed in U.S. Pat. No. 7,276,068, issued on Oct. 2, 2007, entitled "Vessel Sealing Instrument with Electrical Cutting Mechanism", the disclosure of which is herein incorporated by reference in its entirety.

Figure 3:
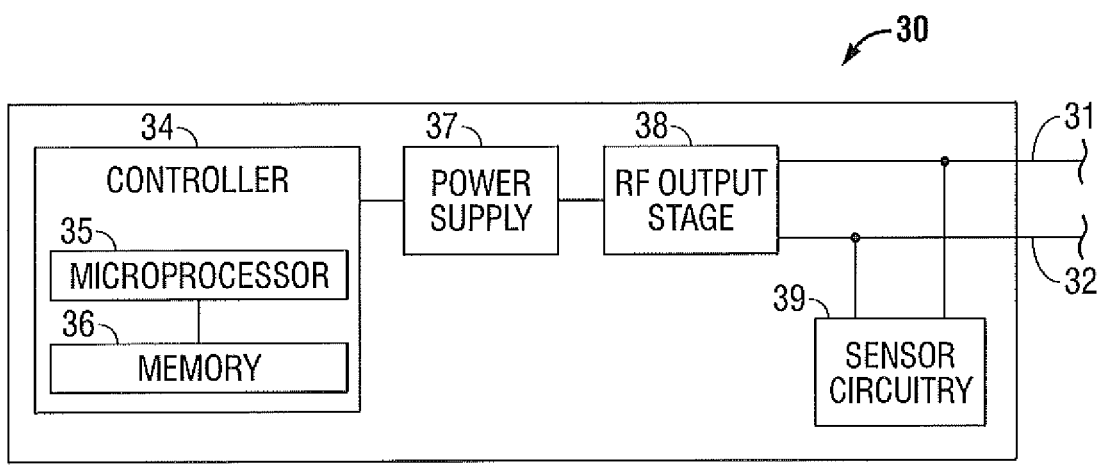
FIG. 3 is a schematic block diagram of a generator in accordance with an embodiment of the present disclosure.

FIG. 3 shows a schematic block diagram of the generator 30 having a controller 34, a DC power supply 37, and an RF output stage 38. The power supply 37 is connected to a conventional AC source (e.g., electrical wall outlet) and is adapted to provide high voltage DC power to an RF output stage 38 that converts high voltage DC power into RF energy. RF output stage 38 delivers the RF energy to an active terminal 31. The energy is returned thereto via the return terminal 32.

The generator 30 may include a plurality of connectors (not shown) to accommodate various types of electrosurgical instruments (e.g., instrument, electrosurgical forceps 10, etc.). Further, the generator 30 may be configured to operate in a variety of modes such as ablation, bipolar cutting, coagulation, sealing, etc. The generator 30 may also include a switching mechanism (e.g., relays) to switch the supply of RF energy between the connectors.

The controller 34 includes a microprocessor 35 operably connected to a memory 36, which may be volatile type memory (e.g., RAM) and/or non-volatile type memory (e.g., flash media, disk media, etc.). The microprocessor 35 is operably connected to the power supply 37 and/or RF output stage 38 allowing the microprocessor 35 to control the output of the generator 30 according to either open and/or closed control loop schemes. Those skilled in the art will appreciate that the microprocessor 35 may be substituted by any logic processor (e.g., control circuit) adapted to perform the calculations discussed herein.

A closed loop control scheme or feedback control loop is provided that includes sensor circuitry 39 having one or more sensors (not shown) for measuring a variety of tissue and energy properties (e.g., tissue impedance, tissue temperature, output current and/or voltage, etc.). The sensor circuitry 39 provides feedback to the controller 34. Such sensors are within the purview of those skilled in the art. The controller 34 then signals the HVPS 37 and/or RF output phase 38 which then adjusts the DC and/or RF power supply, respectively. The controller 34 also receives input signals from the input controls of the generator 30 or the instrument 10. The controller 34 utilizes the input signals to adjust power outputted by the generator 30 and/or performs other control functions thereon.

The forceps 10 is configured to operate in three modes or phases: (1) electrosurgical tissue sealing, (2) bipolar electrosurgical cutting, and (3) duty cycle controlled or modulated waveform bipolar electrosurgical cutting. The third mode or phase is applied when the tissue does not completely separate causing the tissue to have a very high electrical impedance.

Figure 4:
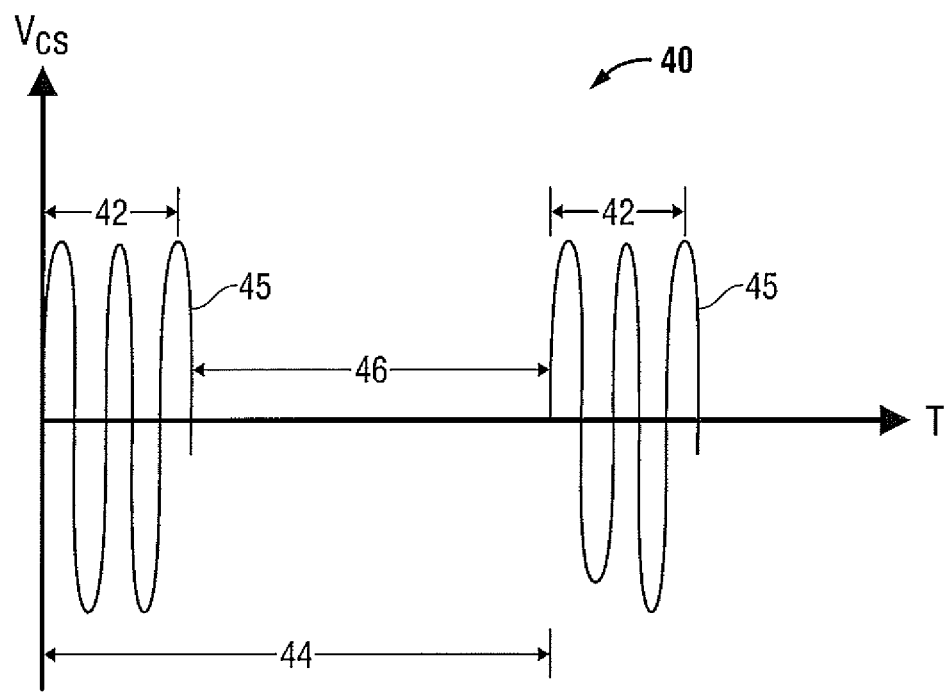
FIG. 4 illustrates a duty cycle controlled waveform according to an embodiment of the present disclosure.

FIG. 4 illustrates a duty cycle controlled waveform 40 for use in the third phase. The waveform 40 is shown with a fundamental frequency 45 and a duty cycle 42, where the duty cycle is the percentage of "on" time in a repetition rate 44. The time difference between pulses is the percentage of "off" time 46 in the repetition rate 44.

The fundamental frequency 45 can range from 424 kHz to 520 kHz. More specifically, the fundamental frequency ranges from 448 KHz to 496 kHz. The duty cycle 42 can range from 5% to 50% of the "on" time in the repetition rate 44, and more specifically from 5% to 20% of the "on" time in the repetition rate 44.

The duty cycle controlled waveform 40 allows for a higher voltage to be applied to the tissue while keeping the RMS power low. A high RMS power may damage the polymers used in the electrodes or cause other undeterminable effects. The duty cycle controlled waveform 40 creates power pulses, where the power and voltage are in an exponential relationship, as shown below:

$$P = V^2/R$$

The power pulses drive power and create heat in the high impedance tissue. The creation of heat mobilizes water content next to the high impedance desiccated tissue. The heating and mobilization of water induces motion in the tissue and aids in complete separation of tissue.

Figure 5A:
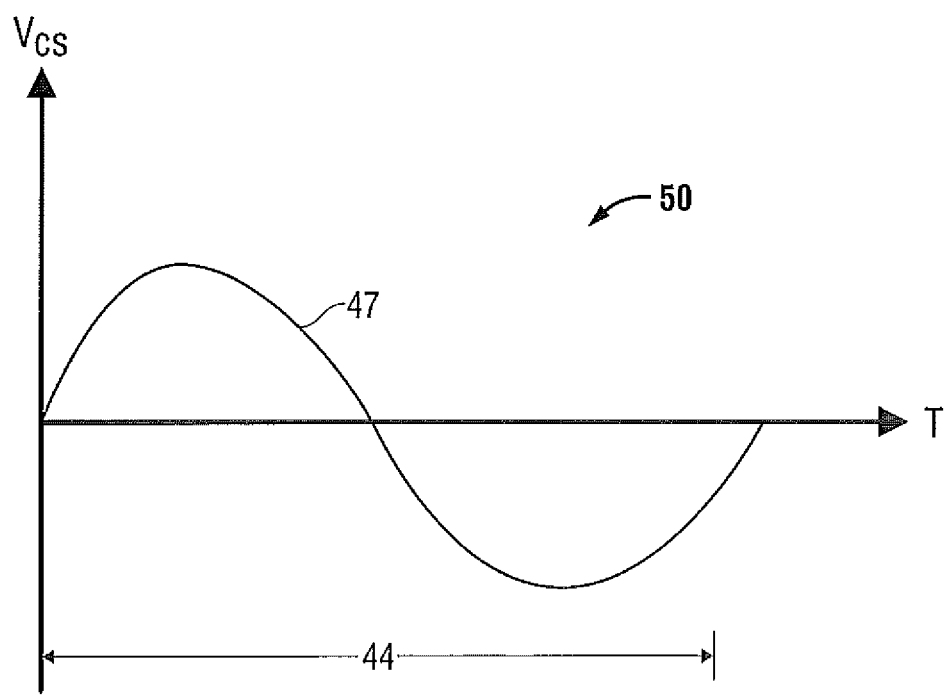
FIG. 5(a) illustrates a beat frequency waveform according to an embodiment of the present disclosure.
Figure 5B:
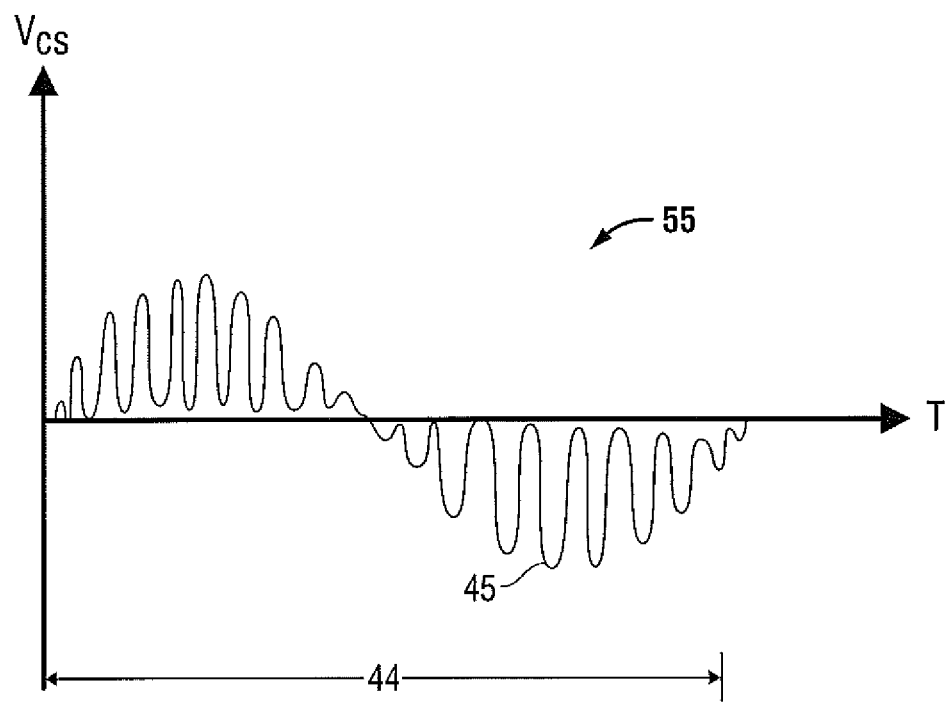
FIG. 5(b) illustrates a fundamental frequency waveform according to an embodiment of the present disclosure.

FIG. 5(*a*) illustrates a beat frequency waveform 50. The beat frequency 47 can range from 0.5 kHz to 20 kHz. FIG. 5(*b*) illustrates a fundamental frequency waveform 55.

Figure 6:
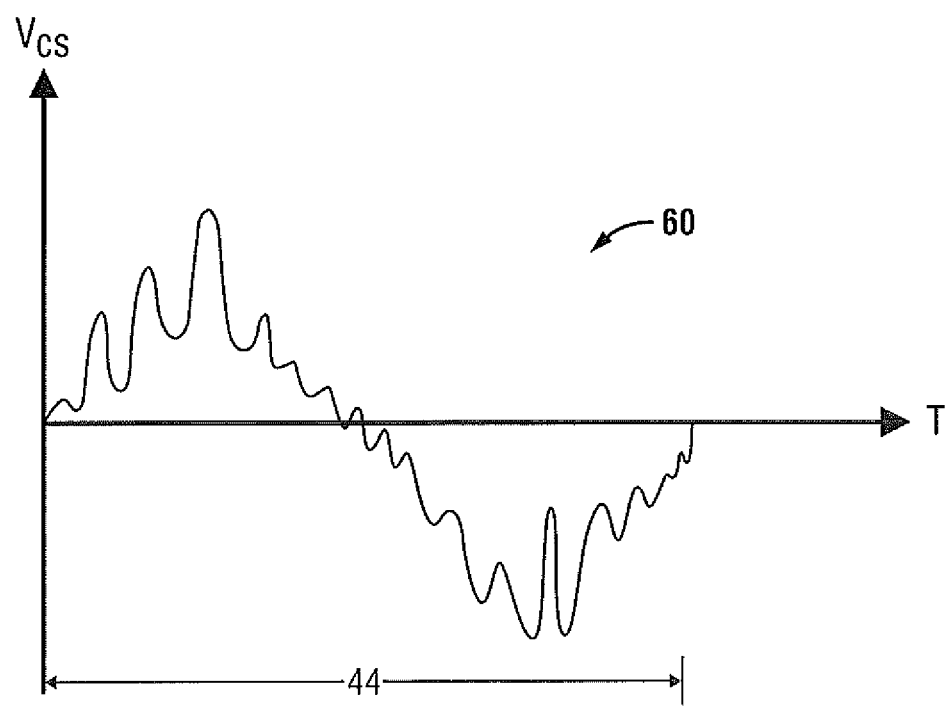
FIG. 6 illustrates a modulated output according to an embodiment of the present disclosure.

Modulated waveform 60 in FIG. 6 illustrates the multiplication of the beat frequency waveform 50 and the fundamental frequency waveform 55. The resulting modulated waveform 60 creates a modulated effect that allows for a more smooth transition of energy delivery. Further, the resulting waveform 50 defines a technique of more complex energy delivery that results in a more destructive arc that improves tissue vaporization. Moreover, the modulated waveform 60 allows for a higher voltage to be applied to the tissue while keeping the RMS power low. The modulated waveform 60 creates power pulses, where the power and voltage are in a exponential relationship. The power pulses drive power and create heat in the high impedance tissue. The creation of heat mobilizes water content next to the high impedance desiccated tissue. The heating and mobilization of water induces motion in the tissue and aids in complete separation of tissue.

In alternative embodiments, the beat frequency waveform 50 and the fundamental frequency waveform 55 can be added together to form a modulated waveform. Additionally, the fundamental frequency waveform 55 can be added or multiplied with itself, a sine wave, a square wave, a triangular wave, a duty cycle controlled waveform, or other waveform. Further, the beat frequency waveform 50 can be added or multiplied with itself, a sine wave, a square wave, a triangular wave, a duty cycle controlled waveform, or other waveform. Additionally, this modality of combining frequencies can be combined with other tissue degradation techniques to optimize the surgical procedure.

Figure 7:
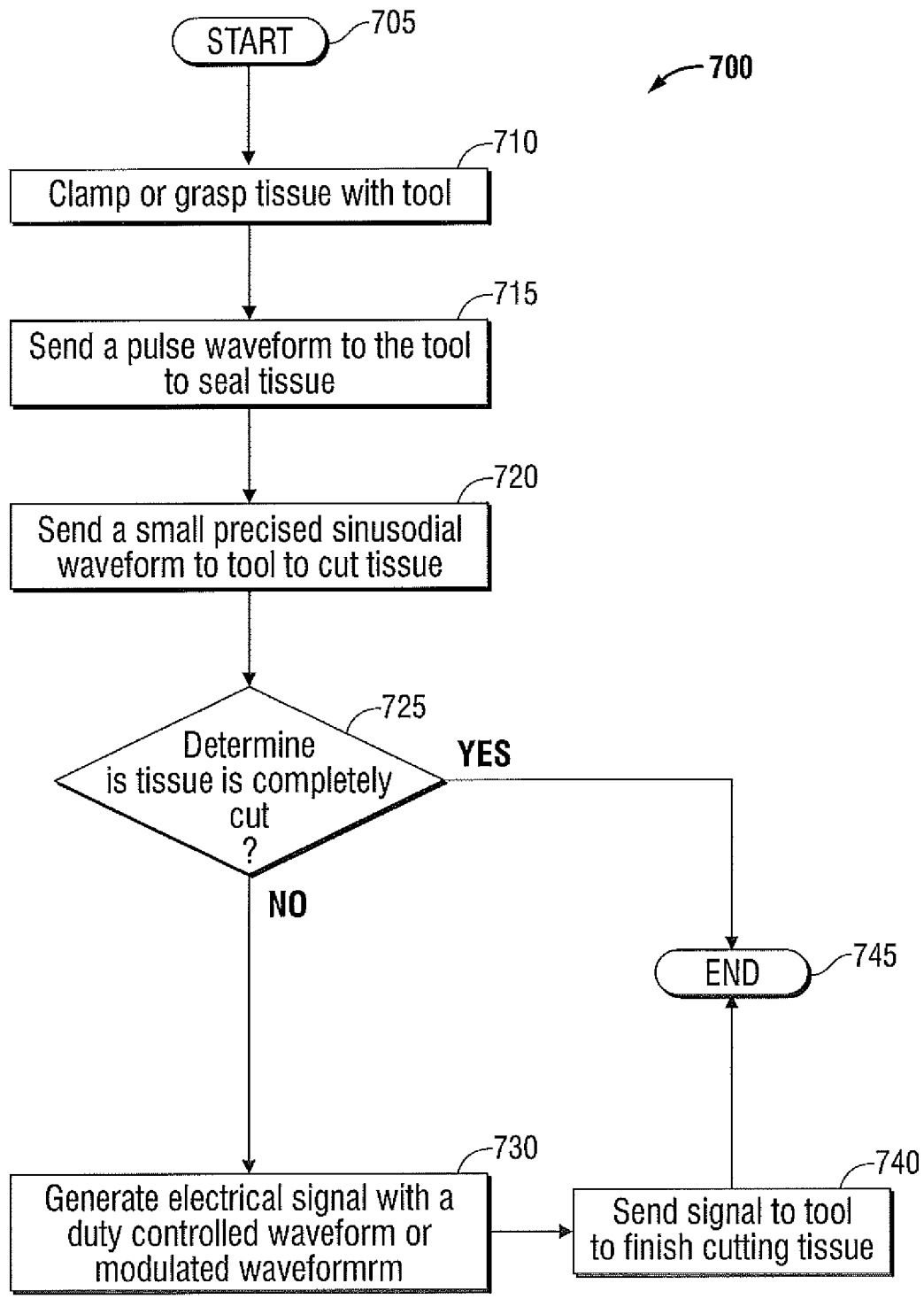
FIG. 7 is a flow diagram of a process for optimizing tissue separation using duty cycle controlled and modulated waveforms according to an embodiment of the present disclosure.

FIG. 7 is a flow diagram of a process 700 for optimizing tissue separation by controlling waveform and duty cycle parameters. The process 700 starts with step 705, which invokes clamping or grasping tissue with the instrument 710. The generator then sends a pulse waveform to the instrument 10 to seal the tissue at step 715. To cut the tissue at step 720, the generator sends a small precise sinusoidal waveform to the instrument. Next, a sensor (not shown) on the instrument 10 and/or sensor circuitry 39 is used to determine if the tissue is completely separated at step 725 by measuring the electrical impedance of the cut tissue. If the sensor circuitry measures a high electrical impedance across the tissue, then the tissue is not completely separated. If the tissue is not completely separated, then the generator generates an electrical signal at step 730 with a duty cycle controlled waveform 40 or a modulated waveform 60. The electrical signal sent in step 730 can automatically be sent by the generator 30 if the tissue is not completely separated in step 720. Alternatively, a user may be prompted that the tissue was not completely separated in step 720. Then, the user may be prompted to initiate the generator 30 to generate the electrical signal in step 730. Then, the generator sends the electrical signal to the instrument 10 to finish cutting the tissue at step 740. The process 700 then ends at step 745 after sending the electrical signal or after determining the tissue is completely separated.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for optimizing tissue separation, the method comprising: grasping a section of tissue with an electrosurgical instrument; sending a pulse waveform to the instrument to seal the tissue; sending a sinusoidal waveform to the instrument to cut the tissue; determining if the tissue is completely separated; in response to determining the tissue is not completely separated, generating a modulated waveform having a larger voltage than the sinusoidal waveform used to cut the tissue and a low root mean square (RMS) power value, wherein the modulated waveform is generated by multiplying a sine wave at a specified beat frequency by a sine wave at a specified fundamental frequency and the beat frequency is from about 0.5 kHz to about 20 kHz; and sending the modulated waveform to the instrument to completely separate the tissue.

2. The method according to claim 1, wherein the fundamental frequency is between about 424 kHz and about 520 kHz.

3. The method according to claim 1, wherein the modulated waveform is generated by adding or multiplying at least two waveforms selected from the group consisting of a parameter specified waveform, a sinusoidal waveform, a triangular waveform, a square waveform, and a duty cycle controlled waveform.

4. The method according to claim 1, wherein the modulated waveform is generated by adding or multiplying two or more sine waves together.

5. The method according to claim 1, wherein the modulated waveform is generated by adding or multiplying a sine wave and a square wave together.

6. The method according to claim 1, wherein the modulated waveform is generated by adding or multiplying a sine wave and a triangle wave together.

7. The method according to claim 1, wherein the fundamental frequency is between about 448 kHz and about 496 kHz.

8. The method according to claim 1, wherein the instrument is a bipolar forceps.

* * * * *